(12) United States Patent
Kerby et al.

(10) Patent No.: US 6,953,433 B2
(45) Date of Patent: Oct. 11, 2005

(54) PROTOCOL CONTROLLER FOR A MEDICAL DIAGNOSTIC IMAGING SYSTEM

(75) Inventors: Cynthia L. Kerby, Carnation, WA (US); Laurence S. McCabe, Sunnyvale, CA (US); David R. DeWitt, Livermore, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 19 days.

(21) Appl. No.: 10/651,374

(22) Filed: Aug. 29, 2003

(65) Prior Publication Data

US 2005/0049493 A1 Mar. 3, 2005

(51) Int. Cl.$^7$ ............................................... A61B 8/00
(52) U.S. Cl. ...................................................... 600/443
(58) Field of Search ................................ 600/437, 443, 600/447; 128/916; 700/11, 28; 705/10, 11, 17, 21, 31, 32, 136

(56) References Cited

U.S. PATENT DOCUMENTS

| | | | | | |
|---|---|---|---|---|---|
| 5,831,612 | A | * | 11/1998 | Stoval et al. | 715/792 |
| 6,139,498 | A | * | 10/2000 | Katsman et al. | 600/443 |
| 6,275,869 | B1 | * | 8/2001 | Sieffert et al. | 719/321 |
| 6,397,098 | B1 | * | 5/2002 | Uber et al. | 600/431 |
| 6,458,081 | B1 | * | 10/2002 | Matsui et al. | 600/437 |
| 6,773,398 | B2 | * | 8/2004 | Ogasawara et al. | 600/437 |
| 6,786,869 | B2 | * | 9/2004 | Hashimoto | 600/437 |
| 2002/0035326 | A1 | * | 3/2002 | Kamiyama | 600/437 |
| 2003/0191389 | A1 | * | 10/2003 | Sano et al. | 600/437 |

OTHER PUBLICATIONS

Acuson Sequoia 512 Ultrasound System, User Manual, cover page, pp. ii, 184, and 186–189 (Apr. 1999).
Acuson Sequoia 512 Ultrasound System, Administrator Manual, cover page, pp. ii–iii, and 39–47 (Apr. 1999).
"Megas GP—Advanced Applications—Image Management System (I.M.S.)," http://www.esaote.com/products/ultrasound/megas/cAdvAppliclmsGP.htm, 1 page (printed Oct. 29, 2002).
"Ultrasound Vivid FiVe," GE Medical Systems, http://www.gemedicalsystems.com/rad/us/products/vivid_5/msuvivid5.html, 2 pages (printed Oct. 29, 2002).
"HP Introduced Advanced Diagnostics for HP SONOS 5500 Echocardiography Ultrasound System," http://pacificwestmedical.com/hewlett_packard.htm, 5 pages (printed Oct. 29, 2002).
"Sonos 5500—Ultraperformance Upgrade," Philips Medical Systems, http://www.medical.philips.com/main/products/ultrasound/cardiology/sonos5500/upgrades, 2 pages (printed Jul. 30, 2003).
"Sonos 5500" Philips Medical Systems, http://www.medical.philips.com/main/products/ultrasound/cardiology/sonos5500/, 1 page (printed Jul. 30, 2003).
"Sonos 5500—Features and Benefits," Philips Medical Systems, http://www.medical.philips.com/main/products/ultrasound/cardiology/sonos5500/features, 1 page (printed Jul. 30, 2003).
"Annex X: Ultrasound Staged Protocol Data Management," 3 pages (undated).

* cited by examiner

Primary Examiner—Francis J. Jaworski (57) ABSTRACT

The embodiments described herein relate to a protocol controller for a medical diagnostic imaging system. In one embodiment, two or more distinct study protocols are active on a medical diagnostic imaging system at the same time. In another embodiment, control of a medical diagnostic imaging system is changed at each stage of a study protocol sequence to optimize study performance. In yet another embodiment, a protocol is created from a collection of macros that control a medical diagnostic imaging system. Other embodiments are provided, and each of the embodiments described herein can be used alone or in combination with one another.

14 Claims, 3 Drawing Sheets

PROTOCOL CONTROLLER FOR A MEDICAL DIAGNOSTIC IMAGING SYSTEM

BACKGROUND

The use of protocols to support a stress echo exam is now standard within the ultrasound industry. The common practice is to step the user through pre-defined series of clip acquisitions that allow the clinician to compare left ventricular motion from a variety of views, with and without stressing the heart. Within the industry, there are some very standard pre-defined protocols (e.g., two-stage exercise stress, four-stage exercise stress, etc.). The Sequoia® Echocardiography Platform offers some degree of user customization of protocol factors such as the number of stages, the number of views, and the clip capture parameters used for each stage/view. Additionally, the Phillips 5500 system extends the protocol concept to imaging parameters in a limited way by providing the ability to remember image parameter settings changed by the user in one stage and then recall those settings in a subsequent stage.

SUMMARY

The present invention is defined by the following claims, and nothing in this section should be taken as a limitation on those claims.

By way of introduction, the embodiments described below relate to a protocol controller for a medical diagnostic imaging system. In one embodiment, two or more distinct study protocols are active on a medical diagnostic imaging system at the same time. In another embodiment, control of a medical diagnostic imaging system is changed at each stage of a study protocol sequence to optimize study performance. In yet another embodiment, a protocol is created from a collection of macros that control a medical diagnostic imaging system. Other embodiments are provided, and each of the embodiments described herein can be used alone or in combination with one another.

The embodiments will now be described with reference to the attached drawings.

DETAILED DESCRIPTION OF THE PRESENTLY PREFERRED EMBODIMENTS

Figure 1:
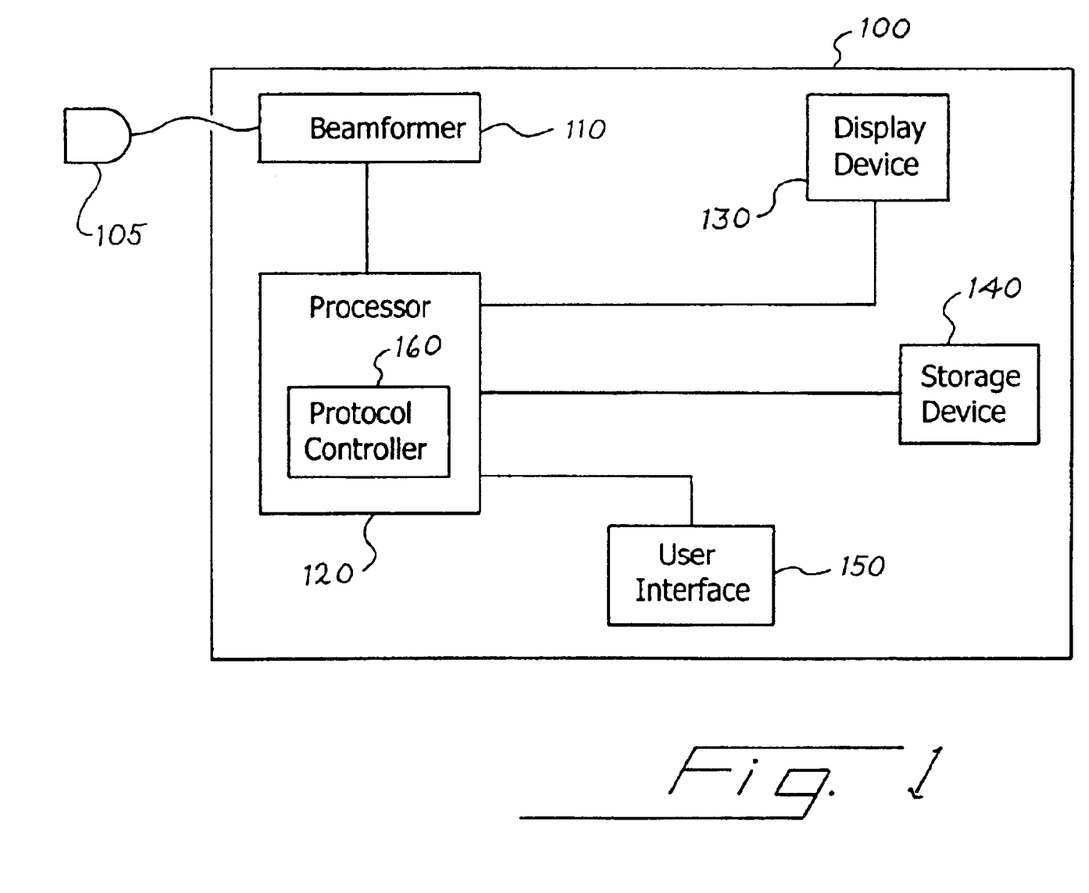
FIG. 1 is a block diagram of a medical diagnostic ultrasound imaging system of an embodiment.

By way of introduction, the embodiments described below relate generally to protocols used in a medical diagnostic imaging system. Although any type of imaging system can be used, these embodiments will be illustrated in conjunction with an ultrasound imaging system. Turning now to FIG. 1, an ultrasound system 100 typically comprises a transducer probe 105, a beamformer 110, a processor 120, a display device 130, a storage device 140, and a user interface 150. The term "processor" is being used to broadly refer to the hardware components and/or software components (i.e., computer-readable program code) of the ultrasound system 100 that are used to implement the functionality described herein. Any suitable hardware/software components can be used. Further, it should be noted that multiple processors can be used and that the functionality described herein can be performed by a single processor or can be distributed among several processors. Additionally, some or all of the functionality described herein can be implemented purely with hardware.

During an ultrasound examination, a sonographer contacts the transducer probe 105 with a patient, and the ultrasound system 100 generates an ultrasound image. In general, the ultrasound system's processor 120 causes the beamformer 110 to apply a voltage to the transducer 105 to cause it to vibrate and emit an ultrasonic beam into the portion of the patient's body in contact with the transducer 105. Ultrasonic energy reflected from the patient's body impinges on the transducer 105, and the resulting voltages created by the transducer 105 are received by the beamformer 110. The processor 120 processes the sensed voltages to create an ultrasound image that is displayed on the display device 130.

The ultrasound system 100 can be used to perform any number of exams (or "studies") of a patient. Some studies require a user to follow a defined "protocol." A "protocol" is a sequence of steps performed by a user (e.g., a sonographer or physician) to perform a particular ultrasound study. A protocol is often used with a "staged" study, although a protocol can also be used with a non-staged study. A staged study contains a set of images acquired under specified conditions during two or more time intervals called "stages" with a consistent set of images called "views" acquired during each stage of the study. The protocol for a staged study dictates the actions a user must perform to complete the study. A user proceeds through a staged protocol exam one stage at a time, acquiring images with the capture settings of each stage. One example of a staged study is a stress echo ultrasound study, which allows a clinician to compare left ventricular motion from a variety of views, with and without stressing the heart. A typical stress echo protocol consists of the user imaging and capturing clips of the patient's heart while the patient's heart is at its resting heart rate. The standard views of the heart that are imaged and captured are Parasternal Long Axis (PLAX), Parasternal Short Axis (PSAX), Apical Four Chamber (A4C), and Apical Two Chamber (A2C). Next, the patient's heart rate is increased to its maximum, either by exercise (e.g., treadmill, bicycle) or with the use of drugs (for those patients who are unable to exercise). The user will image and capture clips (standard views) of the patient's heart while the patient's heart rate is at its maximum increase, before the heart rate slows down (images are typically captured within 60–90 seconds after exercise has stopped). The user reviews the captured clips and selects the clips he wants to keep. The rest of the clips are deleted when the study has ended. The standard has been to capture at least four clips of each view and only keep the best clip for each view of each stage.

An ultrasound imaging system can assist a user in performing a staged protocol study of a patient by automatically controlling various system parameters in accordance with the protocol to guide the user through a pre-defined series of clip acquisitions. For example, an ultrasound system can be programmed with a series of preset, defined protocols (e.g., a two-stage exercise stress echo protocol, a four-stage exercise stress echo protocol, etc.) that a user can select for a particular study. Based on the selected protocol, the ultrasound system automatically moves through stages and views, moves between imaging and review of captured images, provides automatic movement to the next stage, and performs automatic storage and retrieval of each view. The ultrasound system would also know how to capture and playback clips and can automate system actions where appropriate, such as automatically performing a system transition, to help eliminate the number of steps (i.e., button hits) the user must perform, thereby reducing the user's workload.

While some existing ultrasound systems offer some degree of user customization of a protocol (such as the number of stages, the number of views, and the clip capture parameters used for each stage/view or remembering image parameter settings changed by the user in one stage and then recalling those settings in a subsequent stage), the protocol in those systems is for the same application (e.g., a stress echo protocol). In one embodiment, the concept of protocol is expanded beyond its use in stress echo. More generally, the processor 120 in the ultrasound system 100 can be configured to run a protocol controller 160 that allows two or more different protocols to be active simultaneously and be executed together in an integrated fashion. By allowing multiple protocols to be active and work together, imaging modes can be changed in a user-customizable, pre-defined way as the protocol proceeds. This allows the protocol to drive the basic imaging of the system.

For example, an emerging application in ultrasound is the use of contrast agents during imaging. This typically involves imaging the target organ before contrast, injecting contrast media, and imaging the target organ after contrast. At the point of injection, the user often would like to initiate a timer to keep track of elapsed time from injection. During imaging and after contrast injection, a different imaging mode is typically used with a completely different suite of imaging parameters. To document, this procedure, a different set of clip capture parameters are typically used for pre-injection vs. post-injection clips.

By allowing aspects of system operation to be coordinated in a user-customizable, pre-defined way, a user can nest a pre-defined stress echo protocol with a pre-defined contrast protocol to define one integrated protocol that combines the two protocols. In this way, pre-defined protocols can be combined, almost like building blocks, and work together to create new and novel applications. Table 1 shows this combination of stress echo and contrast protocols conceptually, from the user's point of view:

TABLE 1

| User Input | System Response |
| --- | --- |
| Start the "rest" phase of a stress exam. | Initiate the stress protocol. |
| Capture clips to document resting phase without contrast. | Capture clips. |
| Inject contrast media. | Initiate the contrast protocol within the context of the stress echo protocol. |
| Capture clips to document resting phase with contrast. | A new suite of capture parameters is used, optimized for contrast. |
| Move the stress protocol to the next stage: peak exercise. | Return to standard imaging using clip capture parameters optimized for peak stress. |
| Capture clips to document peak stress without contrast. | Capture clips. |
| Inject contrast media. | Initiate the contrast protocol within the context of the stress echo protocol. |
| Capture clips to document resting phase with contrast. | A new suite of capture parameters is used, optimized for contrast. |

The following shows, in more detail, how two different protocols (here, pharmacologic stress echo and contrast) can be active and used together at the same time. Tables 2 and 3 set forth the protocol parameter definition values for pharmacologic stress echo and contrast protocols, and Table 4 provides a description of the actions taken by the user and the ultrasound system's response for each stage in the protocol. It should be noted that this is merely an example, and the details set forth in this example should not be read into the claims.

TABLE 2

Protocol Parameter Definition Values for Pharmacologic Stress Echo Protocol

Stage Sequence: Baseline, Low Dose, Peak Dose
Clip Auto Delete: On
Auto Next Stage: On
Clip Playback Speed: 50%
Clip Playback Mode: Loop aligned
Clip Capture parameter values for Baseline Stage View Sequence: PLAX, PSAX, A4C, A2C
Clips per Capture: 4
Clip Capture Method: Prospective
Compression Rate: Medium
Duration per Clip: 1 heart beat
Clip Auto Review: End of Stage
Clip Capture Size: ¼ ROI
R-Wave Trigger: On
Clip Capture parameter values for Low Dose Stage View Sequence: A2C, A4C, PSAX, PLAX
Clips per Capture: 4
Clip Capture Method: Prospective
Compression Rate: Medium
Duration per Clip: 1 heart beat
Clip Auto Review: End of Stage
Clip Capture Size: ¼ ROI
R-Wave Trigger: On
Clip Capture parameter values for Peak Dose Stage View Sequence: PLAX, PSAX, A4C, A2C
Clips per Capture: Continuous
Clip Capture Method: Prospective
Compression Rate: Medium
Duration per Clip: 1 heart beat
Clip Auto Review: Off
Clip Capture Size: ¼ ROI
R-Wave Trigger: On
Clip Capture parameter values for an Alternate Capture Definition Clips per Capture: 1
Clip Capture Method: Prospective
Compression Rate: Medium
Duration per Clip: 1 minute
Clip Auto Review: Off
Clip Capture Size: ¼ ROI
R-Wave Trigger: Off

TABLE 3

Protocol Parameter Definition Values for Contrast (Sequence for Myocardial Perfusion (MP)) Protocol Trigger: R-wave
Burst Duration: 5 frames (at high MI)
Transmit Duration: Continuous (except during Burst) (at low MI)
Transmit Transition Delay: 0
Restart Sequence after: N + 1, where N = r-wave to r-wave interval
Duration per Clip: 2 heart beats

TABLE 4

| User Input | System Response |
| --- | --- |
| User wants to perform a Stress Echo exam with the use of a Contrast agent. The use of the Contrast agent for MP (myocardial perfusion) is to identify perfusion defects from induced ischemia. The purpose is to document a change in the contrast bubble delivery at rest (patient heart rate at rest) compared with stress (patient heart rate at maximum increase). | The system provides the user with the capability to choose a Stress Echo exam type (exercise or pharmacologic). This example assumes a Pharmacologic Stress Echo exam has been chosen. |
| The user plugs the appropriate cardiac transducer into the system and selects the Pharmacologic Stress Echo exam. | The system performs system initialization for the Stress Echo exam. This entails initializing parameter values for the selected transducer and the Stress Echo exam, such as imaging parameters, calculation package(s), and the Stress Echo protocol. Additionally, it initializes the Contrast protocol, so that a Contrast protocol can be used during a Stress Echo ("SE") exam. The SE Protocol Controller is the current active protocol in the Imaging state, Baseline stage, PLAX view. |
| The user images the patients heart and decides to capture a clip of the heart in BC mode before beginning the Stress Echo - Contrast exam. | |
| The user selects the Alternate Capture via a UI selection, to active the Alternate Capture definitions. The user changes the system from B mode to BC mode. | The system changes the Protocol Clip Capture definitions from the Pharmacologic Stress Echo Protocol Clip Capture definitions to the Pharmacologic Stress Echo Protocol Alternate Capture Clip Capture definitions. (These Alternate Capture definitions allow the user to temporarily capture clips in a non-SE capture method without leaving the SE exam or having to change any Protocol definitions.) |
| The user selects the Clip Capture button to start a Clip capture. | When the Clip Capture button is selected, the system captures 1 Clip (Clips per Capture = 1), where the Clip is up to 1 minute long. The Clip size is full screen (Clip Capture Size = Full Screen). |
| When finished, the user selects the Clip Capture button to stop the Clip capture. | The system will NOT transition from live imaging mode to review (Clip Auto Review = Off) of the clip just captured. |
| The user disables the Alternate Capture, so they can start the SE - Contrast exam. | The system changes the Protocol Clip Capture definitions from the Pharmacologic Stress Echo Protocol Alternate Capture Clip Capture definitions to the Pharmacologic Stress Echo Protocol Clip Capture definitions. |
| The user enables Contrast by selecting the Contrast button and begins image acquisition. | The Contrast Protocol Controller becomes active in addition to the SE Protocol Controller. The Contrast Protocol Controller is in the Normal Acquisition, Sequence 1 state. The system will flow through the SE protocol using the SE protocol defined parameter values and, since Contrast was enabled by selecting the Contrast button, the system will additionally flow through the Contrast protocol using its defined parameter values. Since the parameter 'Duration per Clip' is defined for both protocols, the Contrast value of 2 heart beats will be used. If Contrast was disabled, then the Contrast Protocol Controller would not be active, and its parameter values would not be used. |
| The user injects the patient with the Contrast agent and invokes the Contrast acquisition sequence. | The Contrast protocol acquisition sequence will transmit using the defined parameters above. Every N + 1 (N = 0 initially) heart beats, the system will transmit a burst of 5 frames of high power followed by transmitting low power. |
| The user selects the Clip Capture button to capture clips for each of the 4 views (PLAX, PSAX, A4C, A2C) for the Baseline stage. | Each time the Clip Capture button is selected, the system captures 4 clips (Clips per Capture = 4), where each clip is 2 heart beats long, ¼ ROI size (Duration per Clip = 2 heart beats, Clip Capture Size = ¼ ROI) for all Views (View Sequence) of the Baseline stage. Following the capture of 4 clips for the last view, A2C, the system will transition from live imaging mode to review (Clip Auto Review = End of Stage) of the clips that were captured. |

TABLE 4-continued

| User Input | System Response |
|---|---|
| The user selects the clips he wants to keep, the ones that captured the anatomy clearly. As part of selecting the clip, the user will label the clip with the appropriate View label (i.e., PLAX, etc). | The Protocol Controller knows the View Sequence of this Pharmacologic Stress Echo exam. The protocol will default the clip label to the next View label as the user assigns View labels to their selected clips. |
| The user is ready to continue the exam. The user selects to exit Review and return to live image acquisition. | System transitions from review to live imaging. The SE Protocol Controller is in Imaging state, Low Dose stage, A2C view. |
| The user injects pharmacological drug to increase the patients heart rate. The user injects the patient with the Contrast agent and invokes the Contrast acquisition sequence and begins image acquisition. | The Contrast protocol acquisition sequence will transmit using the defined parameters above. Every $N + 1$ ($N = 0$ initially) heart beats, the system will transmit a burst of 5 frames of high power followed by transmitting low power. |
| The user selects the Clip Capture button to capture clips for each of the 4 views (A2C, A4C, PSAX, PLAX) for the Low Dose stage. | Each time the Clip Capture button is selected, the system captures 4 clips (Clips per Capture = 4) where each clip is 2 heart beats long, ¼ ROI size (Duration per Clip = 2 heart beats, ¼ ROI size) for all Views (View Sequence) of the Low Dose stage. Following the capture of 4 clips for the last view, PLAX, the system will transition from live imaging mode to review (Clip Auto Review = End of Stage) of the clips that were captured. |
| The user selects the clips he wants to keep, the ones that captured the anatomy clearly. As part of selecting the clip, the user will label the clip with the appropriate View label (i.e., PLAX, etc). | The Protocol Controller knows the View Sequence of this Pharmacologic Stress Echo exam. The protocol will default the clip label to the next View label as the user assigns View labels to their selected clips. |
| The user is ready to continue the exam. The user selects to exit Review and return to live image acquisition. | System transitions from review to live imaging. The SE Protocol Controller is in Imaging state, Peak Dose stage, PLAX view. |
| The user increases the injected amount of pharmacological drug to increase the patient's heart rate even higher When the patient's heart rate is where the physician wants it to be, the user injects the patient with the Contrast agent and invokes the Contrast acquisition sequence and begins image acquisition. | The Contrast protocol acquisition sequence will transmit using the defined parameters above. Every $N + 1$ ($N = 0$ initially) heart beats, the system will transmit a burst of 5 frames of high power followed by transmitting low power. |
| The user selects the Clip Capture button once for a continuous capture. This captures clips for each of the 4 views (PLAX, PSAX, A4C, A2C) for the Peak Dose stage. When finished, the user selects the Clip Capture button to stop the Continuous Clip capture. | The system begins a Continuous Clip capture (Clips per Capture = Continuous) where each clip is 2 heart beats long, ¼ ROI size (Duration per Clip = 2 heart beats, ¼ ROI size). The user moves the transducer through all 4 views to capture clips of each view. The system will NOT transition from live imaging mode to review (Clip Auto Review = Off) of the clips that were captured. |
| The user selects Review to view all clips captured for the exam. | The system transitions from live imaging mode to review of the clips that were captured. |
| The user selects the clips he wants to keep, the ones that captured the anatomy clearly. As part of selecting the clip, the user will label the clip with the appropriate View label (i.e., PLAX, etc). | The Protocol Controller knows the View Sequence of this Pharmacologic Stress Echo exam. The protocol will default the clip label to the next View label as the user assigns View labels to their selected clips. |

TABLE 4-continued

| User Input | System Response |
|---|---|
| The user selects to end the exam. | The Protocol Controller was initialized for the Pharmacologic Stress Echo protocol to delete all clips that are not selected as clips to keep at the end of the exam (Clip Auto Delete = On). The clips not selected as clips to keep are deleted when the patient record is closed. |

In the examples set forth above, two different protocols were active and used together at the same time. In a more general embodiment, the concept of nested protocols can be used to automatically change the control of the ultrasound system at each stage of a multi-stage study protocol sequence. Such optimization can be used to improve image quality and study workflow and can involve changing annotations and/or DICOM settings. In this way, nesting two or more different protocols so that a segment of one study protocol is inserted into another study protocol can be viewed as a particular example of changing the control of the ultrasound system at each stage of a multi-stage study protocol sequence.

It is presently preferred that the Protocol Controller 160 be implemented as a software-implemented finite state machine. Of course, other implementations can be used. Finite state machines are known in the art and are described in, for example, chapter 5 of "Dynamic Modeling in Object-Oriented Modeling and Design" by Rumbaugh, Blaha, Premerlani, Eddy and Lorensen, which is hereby incorporated by reference. It is preferred that the finite state machine design pattern be implemented in such a way that the finite state machine software allows the Protocol Controller 160 to implement a state model diagram in a highly configurable way. A state model diagram relates events and states. When an event is received, the next state depends on the current state as well as the event. A change of state caused by an event is called a transition. A state model diagram is a graph whose nodes are states and whose directed arcs are transitions labeled with event names. There can be guards and actions associated with state transitions, as well as state entry and state exit actions. The finite state machine represents a collection of hierarchical states, where only one sub-state is current at any time. An application can have multiple states by having multiple finite state machines. The state model diagram of a given protocol is used to initiate the execution of the application functionality. It is driven by events, which are due to user actions. There can be concurrent finite state machines active at the same time, and they can communicate by sending messages, which may cause state transitions and actions to be executed. The finite state machine model definition is defined in a file using a state model meta-language. This allows a concise definition of all the information represented in the state model diagram. No software coding is required to define the states or their relationships and transitions of the state model diagram. The states and some of their relationships and transitions can be changed without having to recompile and re-build the software.

Each protocol has its own set of parameters that are defined by the protocol and get initialized when the protocol finite state machine is created and initialized. The parameters define to the system how to perform or respond to certain user actions (e.g., selections). The protocol finite state machine always knows what state the protocol is in and defines the sequences of operations that occur in response to external stimuli (e.g., user actions, such as button presses or selections). The external stimuli (user actions) generates system events, and the finite state machine's response to an event depends on the state of the finite state machine receiving the event. It can include a change of state or the sending of another event. The Protocol Controller 160 can have one or more protocol finite state machines created and running concurrently. The protocol finite state machines can send events to each other, so they can be synchronized.

Figure 2:
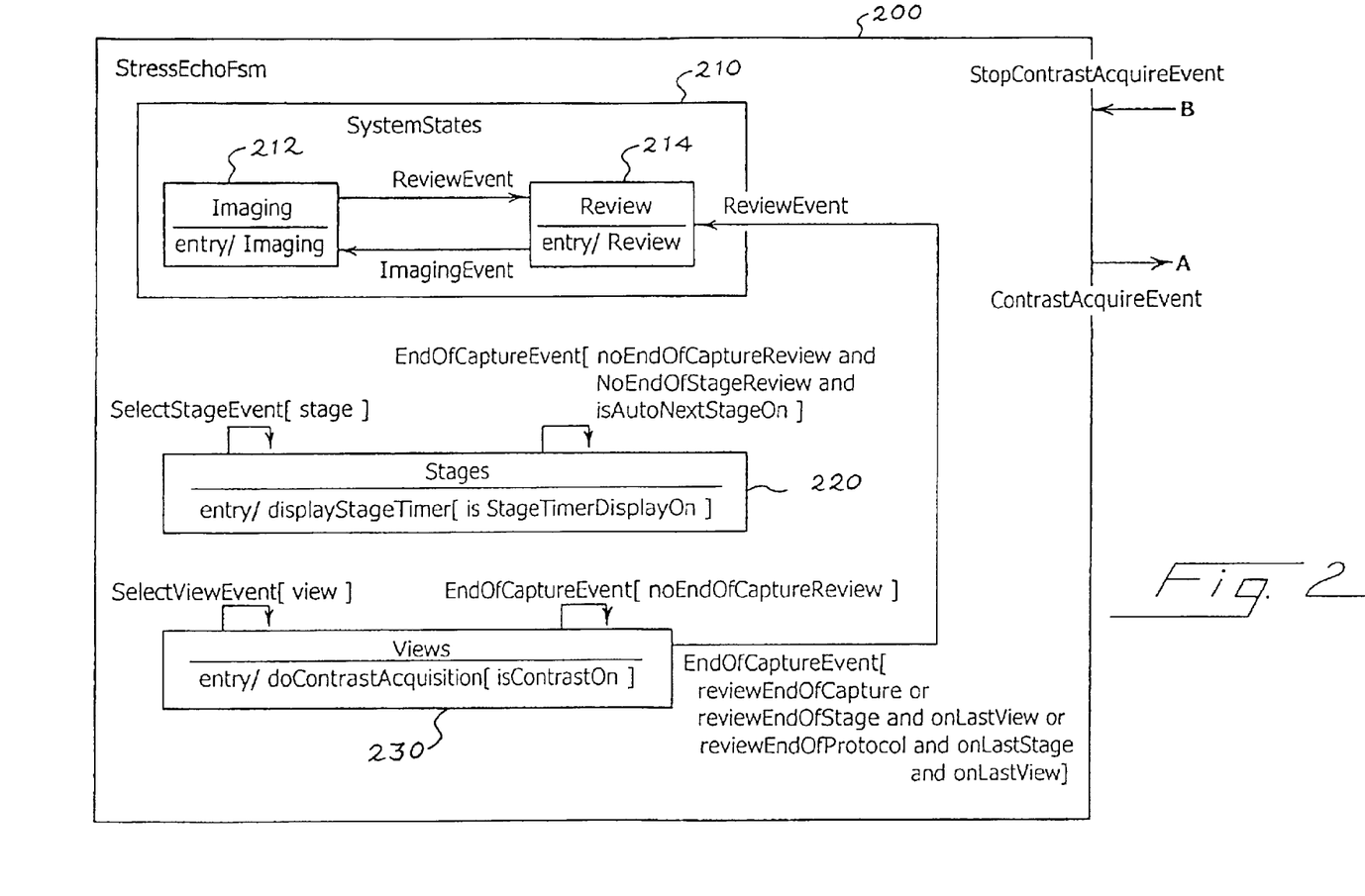
FIG. 2 is a stress echo state transition diagram of an embodiment.
Figure 3:
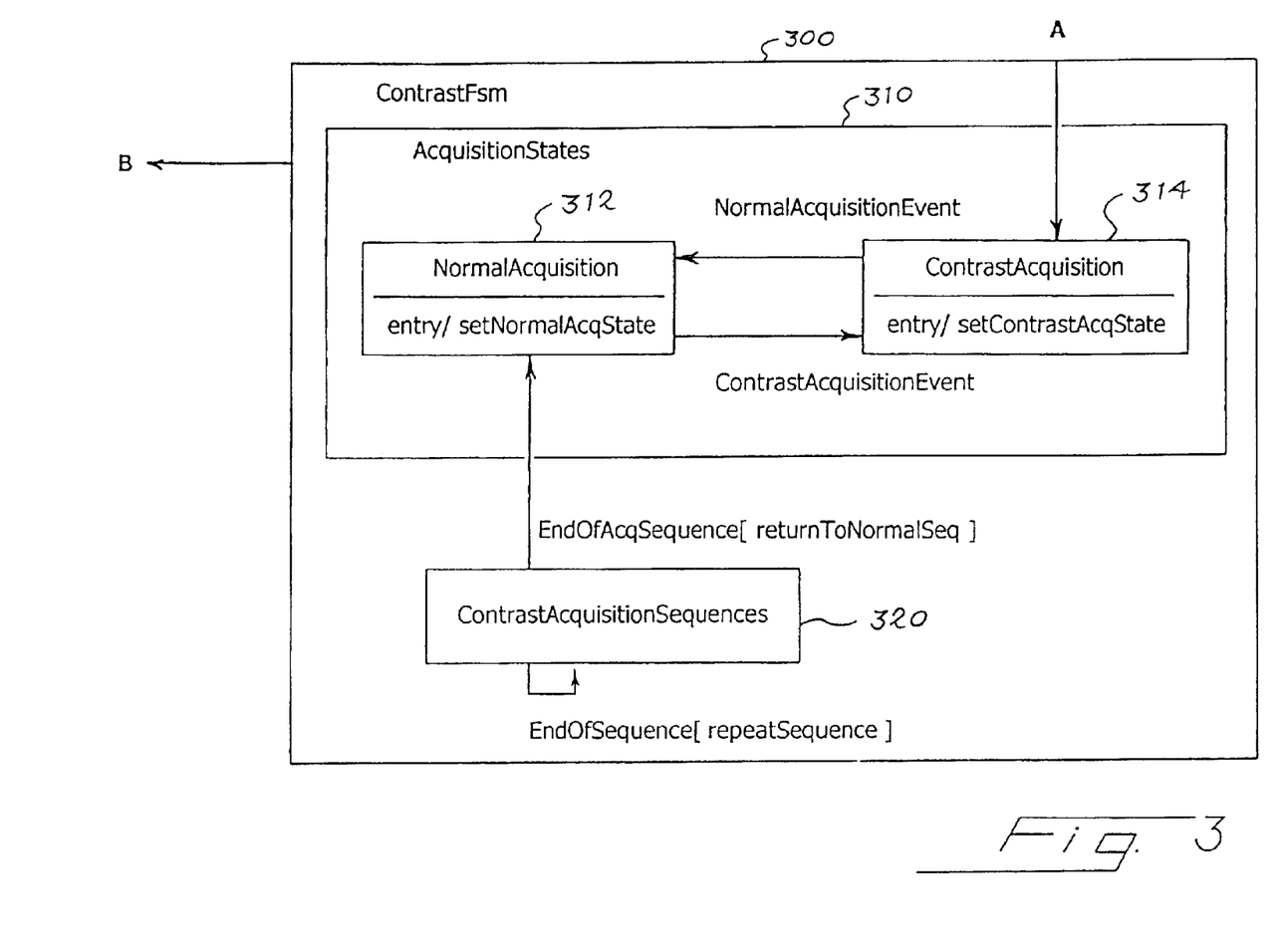
FIG. 3 is a contrast state transition diagram of an embodiment.

FIGS. 2 and 3 are stress echo and contrast state transition diagrams, respectively. In these figures, the lines with arrows represent Events. Events are labeled using "Event" in the name. There are entry functions that get executed as the corresponding state is entered. As events are received, the finite state machine may change states. Events can have guards or action functions. These diagrams show guards and are functions that get called when transitioning to the state. The guard function checks some conditions, such as checking a parameter for a specific value. The guard function must return true before the transition to that state will actually occur (i.e., if the guard function does not return true, then the new state is not entered).

Turning now to FIG. 2, the stress echo protocol finite state machine 200, comprises three concurrent finite state machine: SystemStates 210, Stages 220, and Views 230. The SystemStates finite state machine 210 comprises two states: Imaging 212 and Review 214. The Imaging state 212 is when the system is in live image acquisition, and the Review state 214 is when the system is in review of captured images (still images or multi-frame images (clips)). The Stages finite state machine 220 has as many stages as the system allows. In one embodiment, a maximum of ten stages is used because most stress echo studies will use four to seven stages. Of course, fewer or more stages can be used. These stages correspond with the user stages (e.g., Stage1 would be Baseline, Stage2 would be Low Dose, and Stage 3 would be Peak Dose).

When a Stage is entered, the entry guard function, displayStageTimer, will display the Stage timer if the presets had set the parameter to tell the system to display it; otherwise, it will not be displayed. When the SelectStageEvent is received, it has a parameter of Stage. This tells the finite state machine to go to the Stage passed in. For example, SelectStageEvent(Stage2) tells the finite state machine to go to Stage2. The user would have a selection on the display that would allow him to select a specific stage to go to. That is how this event would be sent out. There could be other ways that the SelectStageEvent gets sent out. When a Clip capture is finished, an EndOfCaptureEvent would be sent out. If the guard functions indicated that the Clip Auto Review parameter was not set to End of Capture or End of Stage and that the Auto Next Stage parameter was set to On, then the finite state machine would automatically move to the next Stage.

View are the same as Stages, only for Views (View1, View2 . . . View 10). As with Stages, a maximum of ten views were selected for this example since most Stress Echo studies use four to six views. These correspond with the user views such as View1 would be the stress echo PLAX view, View2 would be the PSAX view, etc. The entry function, doContrastAcquisition has a guard function of isContrastOn. If contrast is enabled for this view, then the system could automatically activate the Contrast protocol by sending an event (ContrastAcquisitionEvent).

Turning now to FIG. 3, the Contrast protocol finite state machine 300 comprises two concurrent finite state machines: AcquisitionStates 310 and ContrastAquisitionSequences 320. The AcquisitionStates finite state machine 310 has two states: NormalAquisition 312 and ContrastAcquisition 314. The NormalAquisition state 312 is when the system is in live image acquisition and a contrast acquisition sequence is not active. The ContrastAcquisition state 314 is when the system is in live image acquisition and a contrast acquisition sequence is active.

The ContrastAcquisitionSequences finite state machine 319 has as many contrast sequences as desired. There are different ways that the live image acquisition is performed. For example, instead of Normal acquisition where the system just transmits, a contrast sequence may transmit each time the patient's r-wave occurs for some number of r-waves (e.g., 5), and the first transmit may use a high mechanical index (MI), and the subsequent transmissions may use low MI. The purpose being that the first transmit with high MI is to burst the contrast bubbles, and the following transmits are to allow the system to capture an image but not burst any contrast bubbles. This allows the user to see and capture reflow or perfusion of blood into an area in the anatomy (e.g., liver, heart muscle or ventricle).

In another embodiment, a user can select a factory-defined protocol, modify a factory-defined protocol (thereby, making it a user-defined protocol), or create a new protocol. Preferably, the storage device 140 stores a collection of macros for controlling one or more of the following: imaging system settings, the user interface, a display area, and a system peripheral. The processor 120 displays a list of macros on the display device 130 and receives a user selection of two or more of the macros via the user interface 150. The processor 120 then creates a study protocol from the selected macros. In this way, the user can select portions of already-defined protocols (via the list of macros) and put them together to form a new, user-defined group protocol. This eliminates the need for a user to redefine a whole new protocol.

In software, the term "macro" is often used to describe a segment, script, or skeleton that can be used by another process, preferably repeatedly and in more than one way. For example, in Excel, one can build a macro (preferably in Visual C) to perform a sequence of instructions. Once built, the macro can be used repeatedly with a given spreadsheet or moved easily to another spreadsheet and be used there, potentially in a significantly different context. Accordingly, the term "macro" means any sequence of instructions that can be interpreted by another process, causing that process to execute or have executed a sequence of instructions. Macros can be exceedingly useful as building blocks for the Protocol Controller 160. With respect to the Protocol Controller 160, consider a macro to be a set of parameter definitions that define specific ultrasound system behavior. Each macro (or set of parameters) can be used as ultrasound preset data values or ultrasound system controlling parameters. Every protocol will consist of some set of macros. Once a macro has been defined, it belongs to a pool of defined macros. A new protocol can be created by combining a unique set of macros from this pool of already-defined macros. The Protocol Controller 160 itself can then be implemented as an engine used to drive a series of macros. This development is particularly useful in that the engine (i.e., the Protocol Controller 160) can run multiple protocols concurrently and/or one protocol can be suspended, its exit point marked, then another protocol activated, and later return to the exit point of the original protocol and continue with the first protocol. This is illustrated in the above example showing the concurrent use of pharmacologic stress echo and contrast protocols.

Instead of being a set of parameters, a macro can be a code snippet. That is, a macro can be any sequence of instructions that can be interpreted by another process, causing that process to execute a sequence of instructions. In this sense, a "macro" is any sequence of instructions that can be interpreted by another process, causing that process to execute or have executed a sequence of instructions. For example, a protocol can have a data or image capture segment. Each instantiation of capture can be built as a macro, such as "store image to disk" or "store clip to VCR." Of particular usefulness might be an instantiation of a macro for storing data utilizing parameters for a data type and device type: Store <datatype> to <devicetype>. In this way, each segment of the protocol can be written as a macro utilizing parameter. The protocol itself can then be implemented as an engine used to drive a series of macros. This development is particularly useful in that the engine (i.e., the Protocol Controller 160) can be interrupted after execution of a macro, the sequence can be marked to indicate where to re-enter, and the user can run another sequence of macros (protocol) before returning to the exit point and continuing execution of the original protocol.

As mentioned above, the collection of macros controls one or more of the following: imaging system settings, the user interface, a display area, and a system peripheral. More specifically, the macros can control one or more of the following: transmit parameters and settings, receive parameters and settings, imaging mode, imaging parameters and settings, filters and processing specifics, signal processing options, post-processing options, frequency, harmonic, mode, pulse repetition frequency, frame-rate, display control, number of views, annotation, a user interface page displayed in the display area, an active tool displayed in the display area, a cursor in the display area, a number of views in the display area, system control, measurements and reports, annotations, pictograms, review and display features, user preferences, which user interface page is displayed, and which tool/cursor is active, a DICOM device, a CD, a DVD, a VCR, an MO drive, a printer, and a networked device.

Suitable protocol macros include a clip capture macro, a clip playback macro, a workflow macro, and an acquisition sequence macro. The following are examples of these types of macros:

Clip Capture

Number of clips to capture per clip capture activation (1, 2, 4, etc).

Duration/length of each clip to be captured (in seconds, microseconds, heartbeats, etc).

R-wave trigger clip capture enabled/disabled (capture clips based on patients heartbeat or not).

Clip capture delay time (a delay time after an r-wave trigger occurs to start capturing the clip, in microseconds).

Clip compression level.

Clip capture size (full screen, quarter screen, or some other derivative size).

Clip Playback

Clip playback speed.

Clip playback mode (align heartbeats of multiple captured clips or just play each clip or start each clip together at the same time).

Workflow

Enable/disable to automatically delete unselected clips at end of exam.

Enable/disable to automatically move the system to the next stage of a staged protocol.

Enable/disable to automatically start and stop VCR recording based upon some defined event.

Enable/disable to automatically save and recall imaging parameters (a defined set such as transmit/receive settings, imaging mode, filters and processing settings, etc.) upon some defined event such as the first view of each stage of a staged protocol, or at the beginning of a defined acquisition sequence, etc.).

Enable/disable to automatically transfer specifically defined types of data to specifically defined devices or locations, such as transfer clips over the network at the end of each clip capture, transfer still images to a CD at the end of exam, etc.

Enable/disable annotations or pictograms upon the occurrence of some user or system event.

Enable/disable automatically performing a specific measurement upon the occurrence of some user or system event.

Enable/disable entry into a specific measurement and/or report package upon the occurrence of some user or system event.

Enable/disable system guidance, such as a guidance to the user on the next step to perform for a specific type of exam.

Enable/disable to automatically change the imaging mode based upon the occurrence of some user or system event.

Acquisition Sequence

Define a set of imaging acquisition steps where each step would have varying imaging acquisition parameter definitions, the system could automatically move through the acquisition steps or could move through the acquisition steps based upon the occurrence of some user/system event.

In yet another embodiment, an automated exam measurement sequence icon is presented to improve work flow of examinations. Ultrasound systems usually provide a menu for the selection of measurements to be performed during an exam. Once invoked, the menu provides a free-style measurement selection and execution that requires the user to revisit the menu for each successive measurement. However, for the majority of exams, a standard set of measurements are routinely performed in a standard sequence. There may be several such sets of measurements at any specific site or clinic. In this embodiment, an ultrasound system provides an icon that represents an automated sequence of exam measurement. The icon and associated keys provide user control of the sequence including pause, repeat, and skip capabilities. The icon displays the name of the currently active measurement and a tool tip that displays the next measurement in the sequence.

Upon invocation, a menu is displayed that allows the user to select a particular sequence (e.g., a uterus or abdominal sequence). When a sequence is selected from the menu, the first measurement of the sequence is started (i.e., the system enters the proper measurement state and the appropriate measurement tool(s) are displayed). The user then performs the measurement. Once the measurement is completed and its value committed, the next measurement in the sequence begins. A sequence may be terminated by completing the sequence or by repeating the action that invoked the sequence (e.g., pressing the auto-sequence key). Setup facilities allow the user to customize the sequences by changing the order of measurements and by adding or removing measurements. The setup facilities provide for any number of sequences to be stored in memory, each with a specific name that is displayed on the sequence selection menu. The user may also designate a particular subset of the sequences to be displayed on the menu, along with the order in which they appear.

While a sequence is active, the icon displays the name of the current measurement. When the cursor is moved over the icon, a tool tip appears that displays the name of the next measurement in the sequence, and the cursor is changed to the shape of a hand with the index finger pointing to the right. This represents skipping directly to the next measurement in the sequence if the cursor is clicked. If the cursor is instead moved to the left, the cursor changes to a hand with the index finger pointing to the left, indicating a repeat of the previous measurement, and the tool tip text changes to the name of the previous measurement. A double click on the icon at any point pauses the sequence. During a pause, the user may take any actions or measurements desired. The sequence is resume by double clicking on the icon. The icon will change in a recognizable way to indicate that the sequence is paused (e.g., change color).

A dedicated key on the ultrasound console may be used to invoke the auto sequence icon. In this case, pressing the key during a sequence will terminate the sequence. The sequence menu may also be invoked by another menu on the ultrasound system. As an alternative to, or in addition to, the above cursor behavior, a set of console buttons may be used to advance, repeat, and pause the sequence. In addition to measurements, the auto sequences may also include prompts for the user to adjust the transducer or make adjustments to the machine state or image settings, etc.

As noted above, each of the embodiments described herein can be used alone or in combination with one another. As also noted above, these embodiments can be used with image modalities other than ultrasound imaging, and the claims should not be limited to any particular type of image modality unless explicitly recited therein. Examples of different types of image modalities that can be used with these embodiments include, but are not limited to, computed tomography (CT), magnetic resonance imaging (MRI), computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy.

It is intended that the foregoing detailed description be understood as an illustration of selected forms that the invention can take and not as a definition of the invention. It is only the following claims, including all equivalents, that are intended to define the scope of this invention.

What is claimed is:

1. A medical diagnostic imaging system comprising:

a storage device storing a plurality of study protocols for directing an operation of the medical diagnostic imaging system during a medical examination, each study protocol comprising a respective sequence of steps performed by a user to perform a particular study; and a processor operative to have at least two distinct study protocols active at the same time;

wherein the processor is further operative to:

suspend a first study protocol prior to its completion;

activate a second study protocol; and after processing one or more steps of the second study protocol, return to the first study protocol and continue operation from a point at which the first study protocol was suspended.

2. The invention of claim 1, wherein one of the first and second study protocols comprises a stress echo protocol and the other comprises a contrast protocol.

3. The invention of claim 1, wherein the medical diagnostic imaging system comprises an ultrasound imaging system.

4. The invention of claim 1, wherein the processor implements a finite state machine.

5. The invention of claim 1, wherein the medical diagnostic imaging system further comprises a display device, and wherein the processor is further operative to display an icon on the display device that represents an automated sequence of exam measurements, wherein the icon displays a name of a currently active measurement and a tool tip that displays a next measurement in the sequence.

6. The invention of claim 1, wherein at least one of the study protocols comprises a staged protocol.

7. The invention of claim 1, wherein at least one of the study protocols comprises a non-staged protocol.

8. The invention of claim 1, wherein the medical diagnostic imaging system further comprises:

a user interface; and wherein said plurality of study protocols is comprised of a collection of macros for controlling one or more of the following: imaging system settings, the user interface, a display area on a display device, and a system peripheral.

9. The invention of claim 8, wherein the processor is further operative to receive user selection of two or more macros via the user interface and create a study protocol from the selected macros.

10. The invention of claim 9, wherein the collection of macros comprises at least one of the following: a clip capture macro, a clip playback macro, a workflow macro, and an acquisition sequence macro.

11. The invention of claim 9, wherein at least one of the macros controls one or more of the following: transmit parameters and settings, receive parameters and settings, imaging mode, imaging parameters and settings, filters and processing specifics, signal processing options, post-processing options, frequency, harmonic, mode, pulse repetition frequency, and frame-rate.

12. The invention of claim 9, wherein at least one of the macros controls one or more of the following: display control, number of views, annotation, a user interface page displayed in the display area, an active tool displayed in the display area, a cursor in the display area, and a number of views in the display area.

13. The invention of claim 9, wherein at least one of the macro; control; one or more of the following: system control, measurements and reports, annotations, pictograms, review and display features, user preferences, which user interface page is displayed, and which tool/cursor is active.

14. The invention of claim 9, wherein at least one of the macros controls one or more of the following: a DICOM device, a CD, a DVD, a VCR, an MO drive, a printer, and a networked device.

* * * * *